United States Patent
Tapani Kiukkonen (10) Patent No.: US 12,426,800 B2
(45) Date of Patent: Sep. 30, 2025

(54) DETECTING INCREASING FLUID IN A LUNG OF A SUBJECT

(71) Applicant: Nokia Technologies Oy, Espoo (FI)

(72) Inventor: Niko Tapani Kiukkonen, Veikkola (FI)

(73) Assignee: Nokia Technologies Oy, Espoo (FI)

( * ) Notice: Subject to any disclaimer, the term of this patent is extended or adjusted under 35 U.S.C. 154(b) by 1197 days.

(21) Appl. No.: 16/765,102

(22) PCT Filed: Nov. 13, 2018

(86) PCT No.: PCT/EP2018/081115
§ 371 (c)(1),
(2) Date: May 18, 2020

(87) PCT Pub. No.: WO2019/101581
PCT Pub. Date: May 31, 2019

(65) Prior Publication Data
US 2020/0345265 A1    Nov. 5, 2020

(30) Foreign Application Priority Data
Nov. 22, 2017    (EP) .................................... 17203180

(51) Int. Cl.
*A61B 5/08* (2006.01)
*A61B 5/00* (2006.01)
(Continued)

(52) U.S. Cl.
CPC .................. *A61B 5/08* (2013.01); *A61B 5/33* (2021.01); *A61B 5/4878* (2013.01);
(Continued)

(58) Field of Classification Search
CPC ........... A61B 5/08; A61B 5/33; A61B 5/4878; A61B 5/6823; A61B 5/746; A61B 5/0803;
(Continued)

(56) References Cited

U.S. PATENT DOCUMENTS

| 5,109,863 A | 5/1992 | Semmlow et al. |
| 5,957,866 A | 9/1999 | Shapiro et al. |

(Continued)

FOREIGN PATENT DOCUMENTS

WO    2011/093991 A1    8/2011

OTHER PUBLICATIONS

Peacock et al., "Current Technique of Fluid Status Assessment", Congestive Heart Failure, vol. 16, No. 4, Jul.-Aug. 2010, pp. S45-S51.

(Continued)

*Primary Examiner* — Navin Natnithithadha
(74) *Attorney, Agent, or Firm* — McCarter & English, LLP (57) ABSTRACT

A method of detecting increasing fluid in a lung of a subject, the method comprising: at a first time, determining a first difference between a time of arrival of a first feature of a received electrical signal of a subject's heart beat and a time of arrival of a second feature of a received acoustic signal of the subject's heart beat; at a second later time, determining a second difference between a time of arrival of the first feature of a received electrical signal of a subject's subsequent heart beat and a time of arrival of the second feature of a received acoustic signal of the subject's subsequent heart beat; and if the second difference is less than the first difference by more than a threshold value, producing a fluid detection alert.

19 Claims, 3 Drawing Sheets

(51) Int. Cl.
  *A61B 5/33* (2021.01)
  *A61B 7/00* (2006.01)
(52) U.S. Cl.
  CPC ............ *A61B 5/6823* (2013.01); *A61B 5/746* (2013.01); *A61B 5/0803* (2013.01); *A61B 7/00* (2013.01); *A61B 2562/0204* (2013.01)
(58) Field of Classification Search
  CPC ... A61B 7/00; A61B 2562/0204; A61B 5/352; A61B 5/0809; A61B 2505/07
  See application file for complete search history.

(56) References Cited

U.S. PATENT DOCUMENTS

| | | | |
|---|---|---|---|
| 6,527,729 B1 | 3/2003 | Turcott | |
| 6,643,548 B1 | 11/2003 | Mai et al. | |
| 6,931,272 B2 | 8/2005 | Burnes | |
| 7,899,522 B1* | 3/2011 | Koh | A61B 5/349 600/513 |
| 9,351,647 B2 | 5/2016 | Zhang et al. | |
| 2004/0220632 A1* | 11/2004 | Burnes | A61B 5/366 607/9 |
| 2004/0260188 A1 | 12/2004 | Syed et al. | |
| 2006/0106322 A1 | 5/2006 | Arand et al. | |
| 2007/0135725 A1* | 6/2007 | Hatlestad | A61N 1/3627 600/529 |
| 2008/0013747 A1* | 1/2008 | Tran | A61B 7/04 381/67 |
| 2010/0198308 A1* | 8/2010 | Zhou | A61N 1/36521 607/62 |
| 2010/0298899 A1* | 11/2010 | Donnelly | A61N 1/36585 607/6 |
| 2013/0197597 A1* | 8/2013 | Anderson | A61B 5/0538 600/509 |
| 2013/0231711 A1* | 9/2013 | Kaib | G16H 20/30 607/5 |
| 2016/0066801 A1 | 3/2016 | Kahlert et al. | |
| 2016/0213348 A1 | 7/2016 | Reineke et al. | |
| 2016/0354032 A1 | 12/2016 | Wariar | |
| 2017/0119255 A1 | 5/2017 | Mahajan et al. | |
| 2017/0143977 A1 | 5/2017 | Kaib et al. | |
| 2017/0188978 A1* | 7/2017 | Kale | A61B 5/02028 |
| 2020/0345265 A1* | 11/2020 | Tapani Kiukkonen | A61B 5/08 |

OTHER PUBLICATIONS

Potdar et al., "A Review Based Design and Implementation of Electronic Stethoscope for Heart Sound Analysis", International Journal of Engineering Development and Research, 2015, pp. 1057-1064.
"AUDICOR® Technology and Services", Inovise, Retrieved on May 1, 2020, Webpage available at : http://www.inovise.com/products.
Jeon et al., "Implementation of a Portable Device for Real-Time ECG Signal Analysis", BioMedical Engineering OnLine, vol. 13, No. 60, 2014, pp. 1-13.
"VitalPatch", VitalConnect, Retrieved on May 1, 2020, Webpage available at : https://vitalconnect.com/solutions/vitalpatch/.
"Digital Stethoscope, A Portable, Electronic Auscultation Device", Electrical and Computer Engineering, Retrieved on May 1, 2020, Webpage available at : https://people.ece.cornell.edu/land/courses/ece4760/FinalProjects/s2012/ myw9_gdd9/myw9_gdd9/.
"Math of ECGs: Fourier Series", The IntMath, Retrieved on May 1, 2020, Webpage available at : https://www.intmath.com/blog/mathematics/math-of-ecgs-fourier-series-4281.
"Finding Maxima and Minima Values when the Second Derivative is a Constant", Mathematics Stack Exchange, Retrieved on May 1, 2020, Webpage available at : https://math.stackexchange.com/questions/1770302/finding-maxima-and-minima-values-when-the-second-derivative-is-a-constant.
"Tangent Lines And Rates of Change", Paul's Online Notes, Retrieved on May 1, 2020, Webpage available at : http://tutorial.math.lamar.edu/Classes/Calcl/Tangents_Rates.aspx.
"Slope", Wikipedia, Retrieved on May 1, 2020, Webpage available at : https://en.wikipedia.org/wiki/Slope.
Extended European Search Report received for corresponding European Patent Application No. 17203180.9, dated Feb. 19, 2018, 10 pages.
Sharma, "Signal Processing Techniques used for Analysis of Acoustic Signals from Heart and Lungs to Detect Pulmonary Edema in 2015", Thesis, 2015, 128 pages.
Samson, "Changes in Systolic Time Intervals in Acute Myocardial Infarction", British Heart Journal, vol. 32, No. 6, 1970, pp. 839-846.
International Search Report and Written Opinion received for corresponding Patent Cooperation Treaty Application No. PCT/EP2018/081115, dated Dec. 19, 2018, 17 pages.
Office action received for corresponding Indian Patent Application No. 202047024771, dated Jun. 9, 2021, 7 pages.

* cited by examiner

DETECTING INCREASING FLUID IN A LUNG OF A SUBJECT

RELATED APPLICATION

This application claims priority to PCT Application No. PCT/EP2018/081115, filed on Nov. 13, 2018, which claims priority to European Application No. 17203180.9, filed on Nov. 22, 2017, each of which is incorporated herein by reference in its entirety.

TECHNOLOGICAL FIELD

Embodiments of the present invention relate to detecting increasing fluid in a lung of a subject.

BACKGROUND

It is desirable to be able to detect when fluid in a subject's lung is increasing so that, for example, medication may be provided to the subject.

BRIEF SUMMARY

According to various, but not necessarily all, embodiments of the invention there is provided an apparatus comprising:

means for determining, at a first time, a first difference between a time of arrival of a first feature of a received electrical signal of a subject's heart beat and a time of arrival of a second feature of a received acoustic signal of a subject's heart beat;

means for determining, at a second later time, a second difference between a time of arrival of the first feature of a received electrical signal of a subject's subsequent heart beat and a time of arrival of the second feature of a received acoustic signal of the subject's subsequent heart beat; and means for producing a fluid detection alert indicative of increasing fluid in a lung of the subject, if the second difference is less than the first difference by more than a threshold value.

In some but not necessary all examples, the apparatus comprises: an external electrode and a sensor configured to remain at the same positions between the first time and the second time, wherein the means for determining, at the first time, a first difference between a time of arrival of the first feature of a received electrical signal of the subject's heart beat and the time of arrival of the second feature of a received acoustic signal of the subject's heart beat is means for determining at the first time, the first difference between the time of arrival of a first feature of the received electrical signal of the subject's heart beat at the external electrode and the time of arrival of the second feature of the received acoustic signal of the subject's heart beat at the sensor;

and wherein the means for determining, at the second time, the second difference between the time of arrival of the first feature of the received electrical signal of the subject's heart beat and the time of arrival of the second feature of the received acoustic signal of the subject's heart beat is means for determining at the second time, the second difference between the time of arrival of the first feature of the received electrical signal of the subject's heart beat at the external electrode and the time of arrival of the second feature of the received acoustic signal of the subject's heart beat at the sensor.

In some but not necessary all examples, the apparatus comprises multiple electrocardiogram (ECG) electrodes and a single acoustic sensor, all of which are configured to remain at the same positions between the first time and the second time, wherein the means for determining, at the first time, a first difference between a time of arrival of the first feature of a received electrical signal of the subject's heart beat and the time of arrival of the second feature of a received acoustic signal of the subject's heart beat is means for determining at the first time, a first difference between the time of arrival of a first feature of the received ECG electrical signal of the subject's heart beat at the ECG electrodes and the time of arrival of the second feature of the received acoustic signal of the subject's heart beat at the single sensor;

and wherein the means for determining, at the second time, the second difference between the time of arrival of the first feature of the received electrical signal of the subject's heart beat and the time of arrival of the second feature of the received acoustic signal of the subject's heart beat is means for determining at the second time, a second difference between the time of arrival of the first feature of a received ECG electrical signal of the subject's heart beat at the ECG electrodes and the time of arrival of the second feature of the received acoustic signal of the subject's heart beat at the single sensor.

In some but not necessary all examples, the sensor is configured to be placed on a lateral portion of the subject's thorax between a mid-clavicular line and one of the axillary lines and at or below the $5^{th}$ intercostal space.

In some but not necessary all examples, the sensor is configured to be positioned with a lower portion of the subject's lung between the sensor and the subject's heart.

In some but not necessary all examples, the apparatus comprises means for detecting the first feature of the received electrical signal of a subject's heart beat and subsequent heart beat by detecting a recognizable part of an electrocardiogram.

In some but not necessary all examples, the apparatus comprises means for detecting the first feature of the received electrical signal of a subject's heart beat and subsequent heart beat by detecting rapid depolarization of the right and left ventricles and means for detecting the second feature of the received acoustic signal of a subject's heart beat and subsequent heart beat by detecting atrioventricular valves closure at beginning of systole.

In some but not necessary all examples, the apparatus comprises means for detecting the second feature of the received acoustic signal of a subject's heart beat and subsequent heart beat by detecting a first peak following an R peak of a QRS complex of the received electrical signal.

In some but not necessary all examples, the apparatus comprises means for detecting the first feature by detecting an inflection point, local maximum, local minimum, gradient of the received electrical signal amongst other inflection points, local maxima, local minima, gradients of the received electrical signal and wherein the second feature is an inflection point, local maximum, local minimum, gradient of the received acoustic signal amongst other inflection points, local maxima, local minima, gradients of the received acoustic signal.

In some but not necessary all examples, the apparatus comprises means for repeatedly determining over a first time interval of multiple heart beats, preceding the first time, a sample of first differences between a time of arrival of the first feature of a received electrical signal of a subject's heart beat and a time of arrival of the second feature of a received acoustic signal of the subject's heart beat; means for processing the sample of first differences to produce the first difference at the first time; and means for repeatedly determining over a second time interval of multiple subsequent heart beats, preceding the second time, a sample of second differences between a time of arrival of the first feature of a received electrical signal of a subject's subsequent heart beat and a time of arrival of the second feature of a received acoustic signal of the subject's subsequent heart beat and means for processing the sample of second differences to produce the second difference at the second time.

In some but not necessary all examples, the means for processing the sample of first differences to produce the first difference at the first time comprises means for averaging the sample of first differences; and the means for processing the sample of second differences to produce the second difference at the second time comprises means for averaging the sample of second differences.

According to various, but not necessarily all, embodiments of the invention there is provided a method of detecting increasing fluid in a lung of a subject, the method comprising: at a first time, determining a first difference between a time of arrival of a first feature of a received electrical signal of a subject's heart beat and a time of arrival of a second feature of a received acoustic signal of the subject's heart beat;

at a second later time, determining a second difference between a time of arrival of the first feature of a received electrical signal of a subject's subsequent heart beat and a time of arrival of the second feature of a received acoustic signal of the subject's subsequent heart beat; and if the second difference is less than the first difference by more than a threshold value, producing a fluid detection alert.

According to various, but not necessarily all, embodiments of the invention there is provided a method comprising: at a first time, determining a first difference between a time of arrival of a first feature of a received electrical signal of a subject's heart beat and a time of arrival of a second feature of a received acoustic signal of a subject's heart beat;

at a second later time, determining a second difference between a time of arrival of the first feature of a received electrical signal of a subject's subsequent heart beat and a time of arrival of the second feature of a received acoustic signal of the subject's subsequent heart beat; and if the second difference is less than the first difference by more than a threshold value, producing a fluid detection alert indicative of increasing fluid in a lung of the subject.

According to various, but not necessarily all, embodiments of the invention there is provided a computer program that when run on a processor enables the processor to: at a first time, determine a first difference between a time of arrival of a first feature of a received electrical signal of a subject's heart beat and a time of arrival of a second feature of a received acoustic signal of a subject's heart beat;

at a second later time, determine a second difference between a time of arrival of the first feature of a received electrical signal of a subject's subsequent heart beat and a time of arrival of the second feature of a received acoustic signal of the subject's subsequent heart beat; and produce a fluid detection alert indicative of increasing fluid in a lung of the subject, if the second difference is less than the first difference by more than a threshold value.

According to various, but not necessarily all, embodiments of the invention there is provided an apparatus comprising:
at least one processor; and
at least one memory including computer program code the at least one memory and the computer program code configured to, with the at least one processor, cause the apparatus at least to perform:

at a first time, determining a first difference between a time of arrival of a first feature of a received electrical signal of a subject's heart beat and a time of arrival of a second feature of a received acoustic signal of the subject's heart beat;

at a second later time, determining a second difference between a time of arrival of the first feature of a received electrical signal of a subject's subsequent heart beat and a time of arrival of the second feature of a received acoustic signal of the subject's subsequent heart beat; and if the second difference is less than the first difference by more than a threshold value, producing an alert.

According to various, but not necessarily all, embodiments of the invention there is provided examples as claimed in the appended claims.

The following portion of this 'Brief Summary' section, describes various features that may be features of any of the various embodiments described in the foregoing portion of the 'Brief Summary' section. The description of a function should additionally be considered to also disclose any means suitable for performing that function.

In some but not necessarily all examples, at the first time and the second time, the electrical signal is received at the same external electrode at the same location on an exterior of the subject and, at the first time and the second time, the acoustic signal is received at the same sensor at the same location on an exterior of the subject. At the first time and the second time, the electrical signal is received, in some but not necessarily all examples, at the same external ECG electrodes at the same location on an exterior of the subject. The sensor is placed, in some but not necessarily all examples, on a lateral portion of the subject's thorax between a mid-clavicular line and one of the axillary lines and at or below the $5^{th}$ intercostal space. The sensor is positioned, in some but not necessarily all examples, with a lower portion of the subject's lung between the sensor and the subject's heart.

In some but not necessarily all examples, the first feature of the received electrical signal of a subject's heart beat and subsequent heart beat is associated with a recognizable part of an electrocardiogram.

In some but not necessarily all examples, the first feature of the received electrical signal of a subject's heart beat and subsequent heart beat is associated with rapid depolarization of the right and left ventricles and wherein the second feature of the received acoustic signal of a subject's heart beat and subsequent heart beat is associated with atrioventricular valves closure at beginning of systole.

In some but not necessarily all examples, the second feature of the received acoustic signal of a subject's heart beat and subsequent heart beat is associated with a first peak following an R peak of a QRS complex of the received electrical signal.

In some but not necessarily all examples, the first feature is an inflection point, local maximum, local minimum, gradient of the received electrical signal amongst other inflection points, local maxima, local minima, gradients of the received electrical signal and wherein the second feature is an inflection point, local maximum, local minimum, gradient of the received acoustic signal amongst other inflection points, local maxima, local minima, gradients of the received acoustic signal.

In some but not necessarily all examples, the method comprises: detecting a time of arrival of a first feature of a received electrical signal of a subject's heart beat by sampling the received electrical signal at a sampling rate greater than 10 khz; and detecting a time of arrival of a second feature of a received acoustic signal of a subject's heart beat by sampling the received acoustic signal at a sampling rate greater than 10 khz In some but not necessarily all examples, at the first time, determining the first difference between a time of arrival of a first feature of a received electrical signal of a subject's heart beat and a time of arrival of a second feature of a received acoustic signal of the subject's heartbeat, comprises:

repeatedly determining over a first time interval of multiple heart beats, preceding the first time, a sample of first differences between a time of arrival of the first feature of a received electrical signal of a subject's heart beat and a time of arrival of the second feature of a received acoustic signal of the subject's heart beat and processing the sample of first differences to produce the first difference at the first time; and wherein, at a second later time, determining a second difference between a time of arrival of the first feature of a received electrical signal of a subject's subsequent heart beat and a time of arrival of the second feature of a received acoustic signal of the subject's subsequent heart beat; comprises: repeatedly determining over a second time interval of multiple subsequent heart beats, preceding the second time, a sample of second differences between a time of arrival of the first feature of a received electrical signal of a subject's subsequent heart beat and a time of arrival of the second feature of a received acoustic signal of the subject's subsequent heart beat and processing the sample of second differences to produce the second difference at the second time. Processing the sample of first differences to produce the first difference at the first time comprises, in some but not necessarily all examples, averaging the sample of first differences. Processing the sample of second differences to produce the second difference at the second time comprises, in some but not necessarily all examples, averaging the sample of second differences. In some but not necessarily all examples, iteration is used. In some but not necessarily all examples the time difference between the first time and the second time is significantly greater than the duration of the first interval or the second interval. In some but not necessarily all examples the time difference between the first time and the second time is a period when a lower power consumption mode or a lower sampling rate mode is operational and wherein the first interval and the second interval are periods when a higher power consumption mode or a higher sampling rate mode is operational.

BRIEF DESCRIPTION

For a better understanding of various examples that are useful for understanding the detailed description, reference will now be made by way of example only to the accompanying drawings in which.

DETAILED DESCRIPTION

Figure 1:
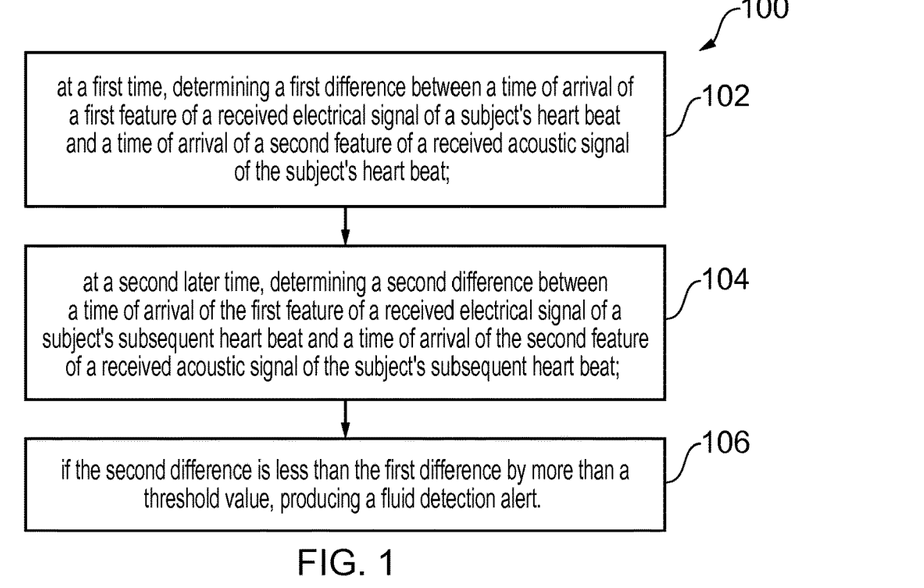
FIG. 1 illustrates an example of a method of detecting increasing fluid in a lung of a subject.

FIG. 1 illustrates an example of a method 100 of detecting increasing fluid in a lung of a subject, the method comprising:

at a first time, at block 102, determining a first difference between a time of arrival of a first feature of a received electrical signal of a subject's heart beat and a time of arrival of a second feature of a received acoustic signal of the subject's heart beat;

at a second later time, at block 104, determining a second difference between a time of arrival of the first feature of a received electrical signal of a subject's subsequent heart beat and a time of arrival of the second feature of a received acoustic signal of the subject's subsequent heart beat; and at block 106, if the second difference is less than the first difference by more than a threshold value, producing a fluid detection alert.

Figure 2:
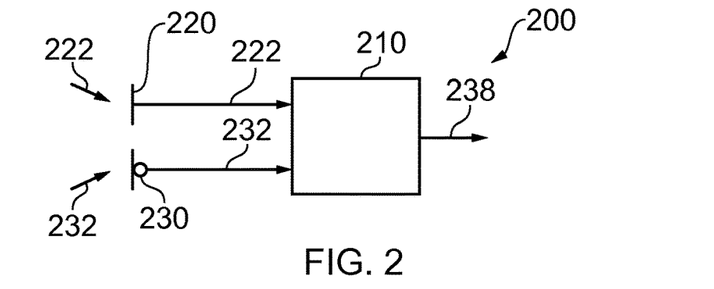
FIG. 2 illustrates an example of an apparatus that provides means for performing the method of FIG. 1.

FIG. 2 illustrates an example of an apparatus 200 that provides means for performing the method of FIG. 1. The apparatus 200 comprises circuitry 210 configured to perform the method 100 of FIG. 1. An electrical signal 222 measured by an electrode 220 is received at the circuitry 210. An acoustic signal 232 measured by a sensor 230 is received at the circuitry 210. The sensor 230 transduces the received pressure waves to an electrical signal. The sensor 230 may, for example, be a microphone. The circuitry 210 produces an alert 238.

The circuitry 210 is configured, at a first time, to determine a first difference between a time of arrival of a first feature (F1) of a received electrical signal 222 of a subject's heartbeat and a time of arrival of a second feature (F2) of a received acoustic signal 232 of the subject's heartbeat. The circuitry is configured, at a second later time, to determine a second difference between a time of arrival of the first feature (F1) of a received electrical signal 222 of a subject's subsequent heartbeat and time of arrival of the second feature (F2) of a received acoustic signal 232 of the subject's subsequent heartbeat.

The circuitry 210 is configured, if the second difference is less than the first difference by more than a threshold value, to produce a fluid detection alert 238.

In some examples, the apparatus 200 is configured to provide the alert 238 as an alert to the subject. In other examples, the apparatus 200 is configured to provide the alert 238 to an apparatus that causes automatic medication of the subject.

In some, but not necessarily all, examples, the apparatus 200 may be a personal device that is worn or carried by the subject.

In some, but not necessarily all, examples, the apparatus 200 may be configured to provide additional functionality. For example, it may produce a visual display of the received electrical signal 222.

Figure 3:
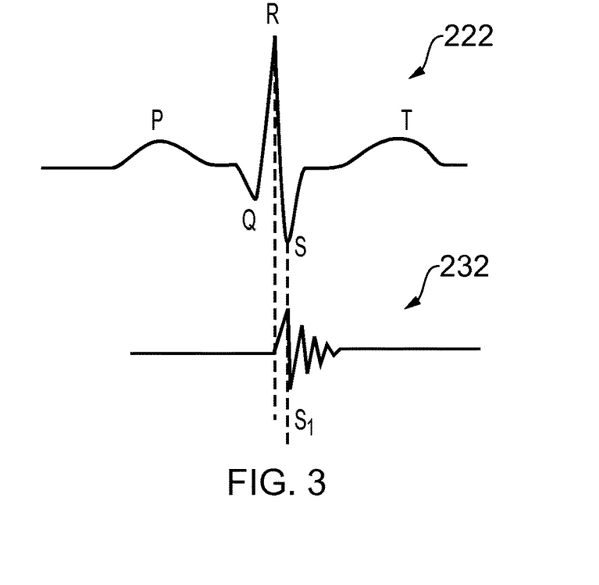
FIG. 3 illustrates an example of a received electrical signal of a subject's heartbeat and a received acoustic signal of the subject's heartbeat.

FIG. 3 illustrates an example of a received electrical signal 222 of a subject's heartbeat and an example of a received acoustic signal 232 of the subject's heartbeat.

In this example, the electrical signal 222 is an electrocardiogram (ECG) signal. An ECG signal has a number of distinct characteristics commonly referred to as PQRST. The P-wave precedes the QRS complex which precedes the T-wave.

Any distinctive feature of the electrical signal 222 may be used as the first feature (F1). The most distinctive feature is the R-peak of the QRS complex. Consequently, the first feature (F1) of the received electrical signal 222 of a subject's heartbeat and the subsequent heartbeat is associated with a recognisable part of an electrocardiogram. For example, it may be associated with rapid depolarisation of the right and left ventricles (R-peak).

In this example, the acoustic signal 232 is a phonocardiogram signal. The phonocardiogram signal 232 has a distinctive maximum amplitude pulse labelled S1.

Any distinctive feature of the acoustic signal 232 may be used as the second feature (F2). The maximum amplitude feature S1 is easily detected.

The second feature of the received acoustic signal 232 of a subject's heartbeat and subsequent heartbeat may be associated with atrioventricular valves closure at beginning of systole.

In some examples, the second feature (F2) of the received acoustic signal 232 of a subject's heartbeat and subsequent heartbeat is associated with the first peak following the R-peak of a QRS complex of the received electrical signal 222.

The first feature and/or second feature may be an inflection point, a local maximum, a local minimum, a gradient of the received signal particularly located amongst other inflection points, local maxima, local minima, gradients of the received signal.

Figure 4A:
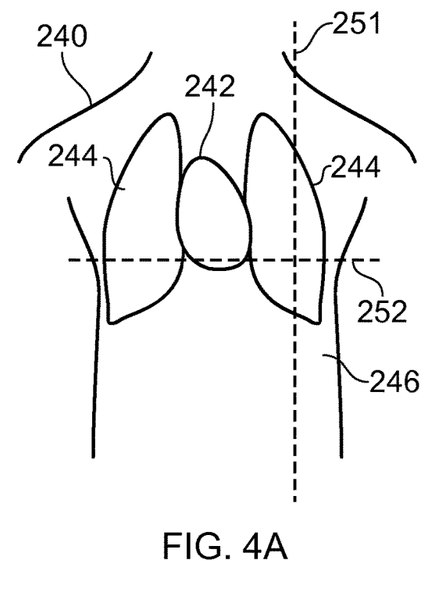
FIGS. 4A and 4B illustrate an example of a subject.
Figure 4B:
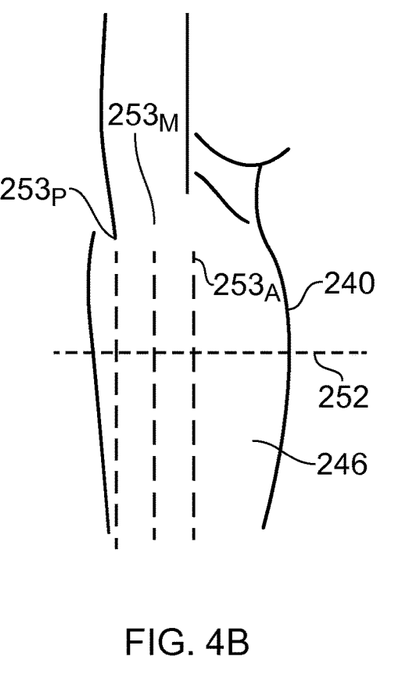

FIGS. 4A and 4B illustrate an example of a subject 240. FIG. 4A illustrates a front (anterior) view and FIG. 4B illustrates a side (lateral) view. The position of the subject's heart 242 and lungs 244 are schematically illustrated in FIG. 4A. The heart 242 is centrally located, slightly to the subject's left. The left lung 244 is posterior to the heart 242.

The ECG electrode 220 may be placed in any suitable position. It may for example be placed in one of the standard positions for obtaining a standard ECG vector.

The sensor 230 for detecting received acoustic signal 232 is preferably positioned with a lower portion of the subject's lung 244 between the sensor 230 and the subject's heart 242.

For example, the sensor 230 may be placed on a lateral portion of the subject's thorax 246 between a mid-clavicular line 251 and one of the axillary lines 253 and at or below the fourth or fifth intercostal space 252. The axillary lines 253 may be any one of the posterior, middle or anterior axillary lines $253_p$, $253_m$, $253_a$.

As previously described, the production of the alert 238 is dependent upon the threshold value. If the second difference is less than the first difference by more than the threshold value then the fluid detection alert 238 is produced. The second difference being less than the first difference may occur because the acoustic signal 232 will propagate through liquid fluid faster than trough air. Therefore when the second difference is less than the first difference by more than the threshold value, the fluid detection alert 238 is likely indicative that there is an increased build-up of liquid fluid at the second time $t_2$ relative to the first time $t_1$. The build-up of liquid fluid may be located within one or both of the subject's lungs 244 and/or in a region of the subject's chest cavity that surrounds the lungs 244.

The threshold value may be subject-dependent. Typically it is of the order 0.2 ms, however, it may vary for different subjects. For example, the threshold value may be based upon the difference between the speed of sound in water/body tissue and speed of sound in air, and the estimated size of the subject's thorax 246. Therefore by measuring the subject's thorax 246 it may be possible to produce a threshold value for that subject. A thorax size may be estimated from a person's height and weight or from chest circumference measurements. Alternatively, it may be desirable to calibrate the apparatus 200 for each subject. For example, calibration may occur by measuring propagation delay of sound through the chest by providing an audio source e.g. a tap (strike) on the outer chest or back.

Figure 5:
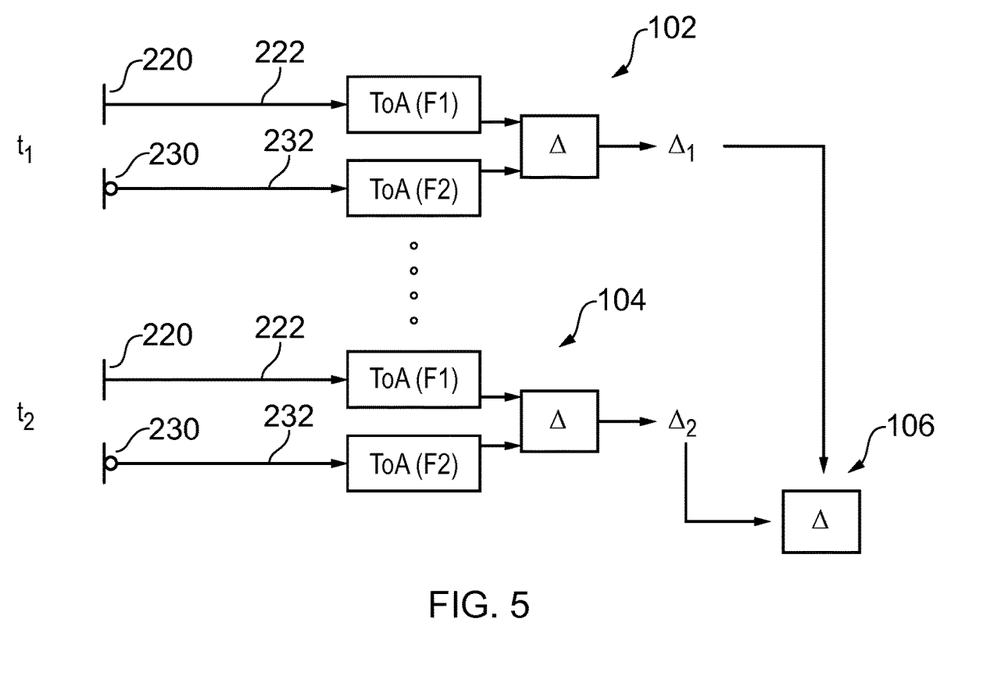
FIG. 5 illustrates an example of an apparatus performing an example of the method of FIG. 1.

FIG. 5 illustrates an example of the apparatus 200 performing the method 100.

At a first time $t_1$, at block 102, the method 100 determines a first difference between a time on arrival of a first feature (F1) of a received electrical signal 222 of a subject's heartbeat and a time of arrival of a second feature (F2) of a received acoustic signal 232 of the subject's heartbeat.

At a second later time $t_2$, at block 104, the method 100 determines the second difference between a time of arrival of the first feature (F1) of a received electrical signal 222 of a subject's subsequent heartbeat and a time of arrival of the second feature (F2) of a received acoustic signal 232 of the subject's subsequent heartbeat.

Then, at block 106, if the second difference is less than the first difference by more than a threshold value, the method 100 produces a fluid detection alert 238.

At the first time $t_1$ and the second time $t_2$, the electrical signal 222 is received at the same external electrode 220 at the same location on an exterior of the subject 240.

At the first time $t_1$ and the second time $t_2$, the acoustic signal 232 is received at the same sensor 230 at the same location on an exterior of the subject 240.

In some, but not necessarily all, examples, only a single sensor 230 for receiving an acoustic signal 232 is required to produce a fluid detection alert 238 for a lung.

In some, but not necessarily all, examples, multiple ECG electrodes 220 may be used.

The time of arrival of a first feature (F1) of a received electrical signal 222 of a subject's heartbeat may be detected by sampling the received electrical signal 222 at a sampling rate greater than 10 khz. A time of arrival of a second feature (F2) of a received acoustic signal 232 of a subject's heartbeat may be detected by sampling the received acoustic signal 232 at a sampling rate greater than 10 khz.

In some, but not necessarily all, examples, the received electrical signal 222 and the received acoustic signal 232 may be sampled using the same clock or synchronised clocks.

There may be a considerable amount of time between the first time $t_1$ and the second time $t_2$ compared to the sample period (100 μs). For example, the time difference may be more than one hour (equivalent to 36 million samples).

In order to improve the accuracy of the method and to avoid the impact of noise, it may be desirable to perform statistical averaging at the first time and to perform, separately, statistical averaging at the second time.

For example, at the first time, at block 102 the method may comprise determining at block 102 a first difference between a time of arrival of a first feature (F1) of a received electrical signal 222 of a subject's heartbeat and a time of arrival of a second feature (F2) of a received acoustic signal of the subject's heartbeat by repeatedly determining over a first time interval $T_1$ of multiple heartbeats, preceding the first time $t_1$ a sample of first differences between the first time of arrival of the first feature (F1) of a received electrical signal 222 of the subject's heartbeat and a time of arrival of the second feature (F2) of a received acoustic signal of the subject's heartbeat and processing the sample of first differences to produce as an average the first difference at the first time. Thus the method of block 102 is applied repeatedly for different heartbeats within the first interval $T_1$ and the resulting first time differences are averaged, although other processes may be used, such as integration, for example.

The method 100 at block 104 may comprise, at the second later time $t_2$, determining a second difference between a time of arrival of the first feature (F1) of a received electrical signal 222 of a subject's subsequent heartbeat and a time of arrival of the second (F2) of a received acoustic signal 232 of the subject's subsequent heartbeat by repeatedly determining over a second time interval $T_2$ of multiple subsequent heartbeats, preceding the second time $t_2$, a sample of second differences between a time of arrival of the first feature (F1) of a received electrical signal 222 of a subject's subsequent heartbeat and a time of arrival of the second feature (F2) of a received acoustic signal 232 of the first subject's subsequent heartbeat and processing the sample of second differences to produce as an average the second difference at the second time. Thus the method of block 102 is applied repeatedly for different heartbeats within the second interval $T_2$ and the resulting second time differences are averaged, although other processes may be used such as integration, for example.

It will be appreciated that, at block 106, the method 100 produces an alert when a difference between the first time of arrival and the second time of arrival decreases, on average, below a threshold.

Figure 6:
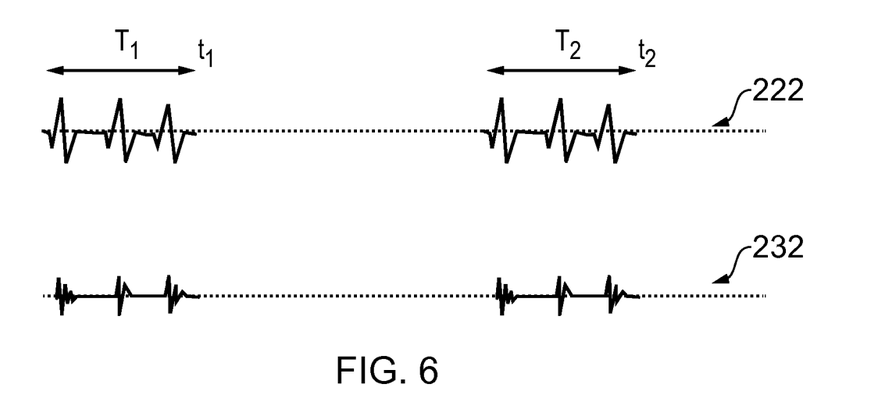
FIG. 6 illustrates an example of an electrical signal and an acoustic signal over a first time interval and a second time interval.

FIG. 6 illustrates an example of the electrical signal 222 and the acoustic signal 232 over the first interval $T_1$ and the second interval $T_2$.

The time difference between the first time $t_1$ and the second time $t_2$ is significantly greater than the duration of the first interval $T_1$ or the second interval $T_2$.

The apparatus 200 may be operated in low power mode between the end of the first interval $T_1$ and the beginning of the second interval $T_2$ and operated at a higher power mode during the first interval $T_1$ and during the second interval $T_2$. Consequently, there is significant power saving compared to continuous operation of the apparatus 200 in the high power mode.

The apparatus 200 may be power downed fully between the end of the first interval T1 and the beginning of the second interval T2

The low power mode may be a mode in which a lower sampling rate is used compared to the higher power mode. The sampling rate of the higher power mode may be above 1 kHz. The sampling rate of the lower power mode may be below 1 kHz.

It will be appreciated that the methods described may be continuously iterated producing comparisons between time of arrival differences determined at any two different times and determining whether or not to produce an alert based on the comparisons. At any arbitrary time $t_n$ the current time may be considered to be the second later time and the immediately preceding time $t_{n-1}$ when the method was performed may be considered to be the first time. It will therefore be appreciated that the method operates continuously.

The averaging over the first time interval and the second time interval is preferably over a time that is long compared to the respiratory cycle. This then normalises the results with respect to the respiratory cycle and results in a consistent comparison of like with like.

Figure 7A:
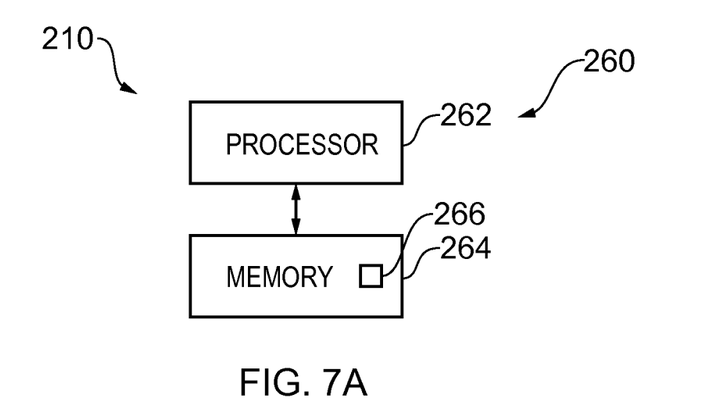
FIGS. 7A and 7B illustrate an example of a controller and a delivery mechanism.

Implementation of the circuitry 210 may be as a controller. The controller may be implemented in hardware alone, have certain aspects in software including firmware alone or can be a combination of hardware and software (including firmware). As illustrated in FIG. 7A such a controller 260 may be implemented using instructions that enable hardware functionality, for example, by using executable instructions of a computer program 266 in a general-purpose or special-purpose processor 262 that may be stored on a computer readable storage medium (disk, memory etc) to be executed by such a processor 262.

The processor 262 is configured to read from and write to the memory 264. The processor 262 may also comprise an output interface via which data and/or commands are output by the processor 262 and an input interface via which data and/or commands are input to the processor 262.

The memory 264 stores a computer program 266 comprising computer program instructions (computer program code) that controls the operation of the apparatus 200 when loaded into the processor 262. The computer program instructions, of the computer program 266, provide the logic and routines that enables the apparatus to perform the methods illustrated in FIGS. 1 and 5. The processor 262 by reading the memory 264 is able to load and execute the computer program 266.

The apparatus 200 therefore comprises:

at least one processor 262; and at least one memory 264 including computer program code the at least one memory 264 and the computer program code configured to, with the at least one processor 262, cause the apparatus 200 at least to perform:

at a first time, determining a first difference between a time of arrival of a first feature of a received electrical signal of a subject's heart beat and a time of arrival of a second feature of a received acoustic signal of the subject's heart beat;

at a second later time, determining a second difference between a time of arrival of the first feature of a received electrical signal of a subject's subsequent heart beat and a time of arrival of the second feature of a received acoustic signal of the subject's subsequent heart beat; and if the second difference is less than the first difference by more than a threshold value, producing a fluid detection alert.

Figure 7B:
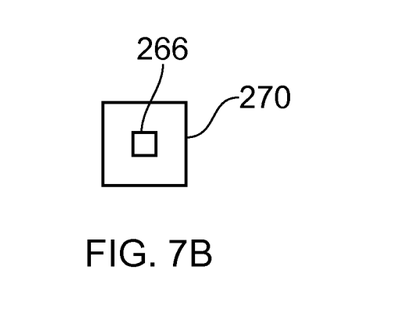

As illustrated in FIG. 7B, the computer program 266 may arrive at the apparatus 200 via any suitable delivery mechanism 270. The delivery mechanism 270 may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 266. The delivery mechanism 270 may be a signal configured to reliably transfer the computer program 266. The apparatus 200 may propagate or transmit the computer program 266 as a computer data signal.

Although the memory 264 is illustrated as a single component/circuitry it may be implemented as one or more separate components/circuitry some or all of which may be integrated/removable and/or may provide permanent/semi-permanent/dynamic/cached storage.

Although the processor 262 is illustrated as a single component/circuitry it may be implemented as one or more separate components/circuitry some or all of which may be integrated/removable. The processor 262 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in the FIGS. 1 and 5 may represent steps in a method and/or sections of code in the computer program 266. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

As used here 'module' refers to a unit or apparatus that excludes certain parts/components that would be added by an end manufacturer or a user.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. An apparatus, comprising:
    at least one processor; and
    at least one memory storing instructions that, when executed with the at least one processor, cause the apparatus at least to perform:
        receiving an acoustic signal of a subject's heart beat from a sensor located on a thorax of the subject;
        receiving an electrical signal of the subject's heart beat from an external electrode located on an exterior of the subject;
        determining, at a first time, a first difference between a time of arrival of a first feature of the received electrical signal of the subject's heart beat and a time of arrival of a second feature of the received acoustic signal of the subject's heart beat;
        determining, at a second later time, a second difference between a time of arrival of the first feature of the received electrical signal of the subject's subsequent heart beat and a time of arrival of the second feature of the received acoustic signal of the subject's subsequent heart beat, wherein the first feature is associated with a rapid depolarization of right and left ventricles of the subject, and wherein the second feature is associated with an atrioventricular valve closure at a beginning of a systole of the subject;
        detecting the second feature of the received acoustic signal of the subject's heart beat and subsequent heart beat by detecting a first peak following an R peak of a QRS complex of the received electrical signal;
        estimating a size of the subject's thorax;

producing a threshold value for the subject based on the estimated size of the subject's thorax, a speed of sound of body tissue, and a speed of sound in air;

comparing, to the threshold value, the second difference between the time of arrival of the first feature of the received electrical signal of the subject's subsequent heart beat and the time of arrival of the second feature of the received acoustic signal of the subject's subsequent heart beat; and producing a fluid detection alert indicative of increasing fluid in a lung of the subject, if the second difference is less than the first difference by more than the threshold value.

2. An apparatus as claimed in claim 1, wherein the external electrode and the sensor are configured to remain at the same positions between the first time and the second time;

wherein the determining, at the first time, a first difference between a time of arrival of the first feature of a received electrical signal of the subject's heart beat and the time of arrival of the second feature of the received acoustic signal of the subject's heart beat is determining at the first time, the first difference between the time of arrival of a first feature of the received electrical signal of the subject's heart beat at the external electrode and the time of arrival of the second feature of the received acoustic signal of the subject's heart beat at the sensor; and wherein the determining, at the second time, the second difference between the time of arrival of the first feature of the received electrical signal of the subject's heart beat and the time of arrival of the second feature of the received acoustic signal of the subject's heart beat is determining at the second time, the second difference between the time of arrival of the first feature of the received electrical signal of the subject's heart beat at the external electrode and the time of arrival of the second feature of the received acoustic signal of the subject's heart beat at the sensor.

3. An apparatus as claimed in claim 2, wherein the sensor is configured to be placed on a lateral portion of the subject's thorax between a mid- clavicular line and one of the axillary lines and at or below a fifth intercostal space.

4. An apparatus as claimed in claim 2, wherein the sensor is configured to be positioned with a lower portion of the subject's lung between the sensor and the subject's heart.

5. An apparatus as claimed in claim 1, comprising multiple electrocardiogram electrodes and a single acoustic sensor, all of which are configured to remain at the same positions between the first time and the second time;

wherein the determining, at the first time, a first difference between a time of arrival of the first feature of a received electrical signal of the subject's heart beat and the time of arrival of the second feature of the received acoustic signal of the subject's heart beat is determining at the first time, a first difference between the time of arrival of a first feature of the received electrocardiogram electrical signal of the subject's heart beat at the electrocardiogram electrodes and the time of arrival of the second feature of the received acoustic signal of the subject's heart beat at the single sensor; and wherein the determining, at the second time, the second difference between the time of arrival of the first feature of the received electrical signal of the subject's heart beat and the time of arrival of the second feature of the received acoustic signal of the subject's heart beat is determining at the second time, a second difference between the time of arrival of the first feature of a received electrocardiogram electrical signal of the subject's heart beat at the electrocardiogram electrodes and the time of arrival of the second feature of the received acoustic signal of the subject's heart beat at the single sensor.

6. An apparatus as claimed in claim 1, wherein the instructions, when executed with the at least one processor, cause the apparatus at least to further perform detecting the first feature of the received electrical signal of the subject's heart beat and subsequent heart beat by detecting a recognizable part of an electrocardiogram.

7. An apparatus as claimed in claim 1, wherein the instructions, when executed with the at least one processor, cause the apparatus at least to further perform:

detecting the first feature of the received electrical signal of the subject's heart beat and subsequent heart beat by detecting depolarization of the right and left ventricles; and detecting the second feature of the received acoustic signal of the subject's heart beat and subsequent heart beat by detecting atrioventricular valves closure at beginning of systole.

8. An apparatus as claimed in claim 1, wherein the instructions, when executed with the at least one processor, cause the apparatus at least to further perform:

detecting the first feature by detecting at least one of an inflection point, local maximum, local minimum, or gradient of the received electrical signal amongst other at least one of inflection points, local maxima, local minima, or gradients of the received electrical signal, and wherein the second feature is at least one of an inflection point, local maximum, local minimum, or gradient of the received acoustic signal amongst other at least one of inflection points, local maxima, local minima, or gradients of the received acoustic signal.

9. An apparatus as claimed in claim 1, wherein the instructions, when executed with the at least one processor, cause the apparatus at least to further perform:

repeatedly determining over a first time interval of multiple heart beats, preceding the first time, a sample of first differences between a time of arrival of the first feature of a received electrical signal of the subject's heart beat and a time of arrival of the second feature of the received acoustic signal of the subject's heart beat;

processing the sample of first differences to produce the first difference at the first time;

repeatedly determining over a second time interval of multiple subsequent heart beats, preceding the second time, a sample of second differences between a time of arrival of the first feature of a received electrical signal of the subject's subsequent heart beat and a time of arrival of the second feature of the received acoustic signal of the subject's subsequent heart beat; and processing the sample of second differences to produce the second difference at the second time.

10. An apparatus as claimed in claim 9, wherein processing the sample of first differences to produce the first difference at the first time comprises averaging the sample of first differences; and wherein processing the sample of second differences to produce the second difference at the second time comprises averaging the sample of second differences.

11. An apparatus as claimed in claim 1, wherein the sensor is a microphone.

12. A method of detecting increasing fluid in a lung of a subject, the method comprising:

receiving an acoustic signal of a subject's heart beat from a sensor located on a thorax of the subject;

receiving an electrical signal of the subject's heart beat from an external electrode located on an exterior of the subject;

at a first time, determining a first difference between a time of arrival of a first feature of the received electrical signal of the subject's heart beat and a time of arrival of a second feature of the received acoustic signal of the subject's heart beat;

at a second later time, determining a second difference between a time of arrival of the first feature of the received electrical signal of the subject's subsequent heart beat and a time of arrival of the second feature of the received acoustic signal of the subject's subsequent heart beat, wherein the first feature is associated with a rapid depolarization of right and left ventricles of the subject, and wherein the second feature is associated with an atrioventricular valve closure at a beginning of a systole of the subject;

detecting the second feature of the received acoustic signal of the subject's heart beat and subsequent heart beat by detecting a first peak following an R peak of a QRS complex of the received electrical signal;

estimating a size of the subject's thorax;

producing a threshold value for the subject based on the estimated size of the subject's thorax, a speed of sound of body tissue, and a speed of sound in air;

comparing, to the threshold value, the second difference between the time of arrival of the first feature of the received electrical signal of the subject's subsequent heart beat and the time of arrival of the second feature of the received acoustic signal of the subject's subsequent heart beat; and if the second difference is less than the first difference by more than the threshold value, producing a fluid detection alert.

13. A method as claimed in claim 12 wherein, at the first time and the second time, the electrical signal is received at the same external electrode at the same location on an exterior of the subject and wherein, at the first time and the second time, the acoustic signal is received at the same sensor at the same location on an exterior of the subject.

14. A method as claimed in claim 13 wherein, at the first time and the second time, the electrical signal is received at the same external electrocardiogram electrodes at the same location on an exterior of the subject and wherein, at the first time and the second time, the acoustic signal is received at the same sensor at the same location on an exterior of the subject, wherein only a single sensor for receiving the acoustic signal is required to produce a fluid detection alert.

15. A method as claimed in claim 12, further comprising detecting the first feature of the received electrical signal of the subject's heart beat and subsequent heart beat by detecting a recognizable part of an electrocardiogram.

16. A method as claimed in claim 12, further comprising detecting the first feature of the received electrical signal of the subject's heart beat and subsequent heart beat by detecting depolarization of the right and left ventricles and detecting the second feature of the received acoustic signal of the subject's heart beat and subsequent heart beat by detecting atrioventricular valves closure at beginning of systole.

17. A non-transitory computer readable medium comprising program instructions stored thereon for performing at least the following:

receiving an acoustic signal of a subject's heart beat from a sensor located on a thorax of the subject;

receiving an electrical signal of the subject's heart beat from an external electrode located on an exterior of the subject;

at a first time, determining a first difference between a time of arrival of a first feature of the received electrical signal of the subject's heart beat and a time of arrival of a second feature of the received acoustic signal of the subject's heart beat;

at a second later time, determining a second difference between a time of arrival of the first feature of the received electrical signal of the subject's subsequent heart beat and a time of arrival of the second feature of the received acoustic signal of the subject's subsequent heart beat, wherein the first feature is associated with a rapid depolarization of right and left ventricles of the subject, and wherein the second feature is associated with an atrioventricular valve closure at a beginning of a systole of the subject;

detecting the second feature of the received acoustic signal of the subject's heart beat and subsequent heart beat by detecting a first peak following an R peak of a QRS complex of the received electrical signal;

producing a threshold value for the subject based on an estimated size of the subject's thorax, a speed of sound of body tissue, and a speed of sound in air;

comparing, to the threshold value, the second difference between the time of arrival of the first feature of the received electrical signal of the subject's subsequent heart beat and the time of arrival of the second feature of the received acoustic signal of the subject's subsequent heart beat; and if the second difference is less than the first difference by more than the threshold value, producing a fluid detection alert.

18. A non-transitory computer readable medium as claimed in claim 17, further comprising program instructions stored thereon for performing at least:

detecting the first feature of the received electrical signal of the subject's heart beat and subsequent heart beat by detecting a recognizable part of an electrocardiogram.

19. A non-transitory computer readable medium as claimed in claim 17, further comprising program instructions stored thereon for performing at least:

detecting the first feature of the received electrical signal of the subject's heart beat and subsequent heart beat by detecting depolarization of the right and left ventricles and detecting the second feature of the received acoustic signal of the subject's heart beat and subsequent heart beat by detecting atrioventricular valves closure at beginning of systole.

* * * * *